(12) United States Patent
Benezra

(10) Patent No.: US 7,247,719 B2
(45) Date of Patent: Jul. 24, 2007

(54) PRIMERS AND PROBES FOR AMPLIFICATION AND DETECTION OF HUMAN INHIBITOR OF DNA-BINDING

(75) Inventor: Robert Benezra, Hampton Bays, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 10/559,062

(22) PCT Filed: Jun. 3, 2004

(86) PCT No.: PCT/US2004/018057

§ 371 (c)(1),
(2), (4) Date: Dec. 1, 2005

(87) PCT Pub. No.: WO2005/001111

PCT Pub. Date: Jan. 6, 2005

(65) Prior Publication Data

US 2006/0134627 A1    Jun. 22, 2006

Related U.S. Application Data

(60) Provisional application No. 60/475,515, filed on Jun. 3, 2003.

(51) Int. Cl.
*C07H 21/04* (2006.01)
*C12Q 1/68* (2006.01)
*C12P 19/34* (2006.01)

(52) U.S. Cl. .................. 536/24.3; 435/6; 435/91.1; 435/91.2

(58) Field of Classification Search .............. None
See application file for complete search history.

(56) References Cited

U.S. PATENT DOCUMENTS 4,530,904 A * 7/1985 Hershberger et al. .......... 435/6

OTHER PUBLICATIONS

Sequence Alignment.*
Acession No. 395337 on electronic database, GenBank, Ellmeier et al., submission Nov. 18, 1993.*
Accession No. 457784 on electronic database, GenBank, Deed et al., submission Jan. 19, 1995.*
Haines et al., "Complex Conserved Organization of the Mammalian Leukemia Inhibitory Factor Gene: Regulated Expression of Intracellular and Extracellular Cytokines," The Journal of Immunology, Apr. 1999, vol. 162, pp. 4637-4646).*
Overdier et al., "The DNA-Binding Specificity of the Hepatocyte Nuclear Factor 3/forkhead Domain Is Influenced by Amino Acid Residues Adjacent to the Recognition Helix," Molecular and Cellular Biology, Apr. 1994, vol. 14, No. 4, pp. 2755-2766.*
Katagiri et al. Identification of a BMP-responsive element in Id1, the gene for inhibition of myogenesis. Genesis to cells, 2002, vol. 7, pp. 949-960.
Biggs et al. A human Id-like helix-loop-helix protein expressed during early development. PNAS. Feb. 1992, vol. 89, pp. 1512-1516.
Ellmeier et al. Mutually exclusive expression of a helix-loop-helix gene and N-myc in human neuroblastomas and in normal development. EMBO J, Jul. 1992, vol. 11, No. 7, Abstract only.

* cited by examiner

*Primary Examiner*—Young J. Kim
(74) *Attorney, Agent, or Firm*—Marina Larson & Associates, LLC

(57) ABSTRACT

Oligonucleotide primers and polynucleotide probes provide selective amplification and detection of Id genetic sequences and are selected both (1) to provide the desired specificity so that they amplify only the specific Id type to which they are targeted; and (2) to introduce terminal restriction endonuclease cleavage sites into the amplicon that facilitate the incorporation of the amplicon into plasmid-based vectors. Detection of Id genetic sequences can be carried out using the labeled-amplicon by reamplifying the amplicon with the primers in the presence of labeled, for example radiolabeled, deoxynucleotide triphosphates. The probes of the invention correspond in sequence to the amplicons produced using the primers of the invention, after cleavage at the restriction endonuclease sites.

3 Claims, No Drawings

SEQUENCE LISTING

<160> NUMBER OF SEQ ID NOS: 9

<210> SEQ ID NO 1
<211> LENGTH: 27
<212> TYPE: DNA
<213> ORGANISM: artificial
<220> FEATURE:
<223> OTHER INFORMATION: primer for human Id protein with inserted
      restriction site

<400> SEQUENCE: 1
ataggatccc accctcaacg gcgagat                                        27

<210> SEQ ID NO 2
<211> LENGTH: 30
<212> TYPE: DNA
<213> ORGANISM: artificial
<220> FEATURE:
<223> OTHER INFORMATION: primer for human Id protein with inserted
      restriction site

<400> SEQUENCE: 2
gtggaattcc ccacagagca cgtaattcct                                     30

<210> SEQ ID NO 3
<211> LENGTH: 28
<212> TYPE: DNA
<213> ORGANISM: artificial
<220> FEATURE:
<223> OTHER INFORMATION: primer for human Id protein with inserted
      restriction site

<400> SEQUENCE: 3
ataggatccc cgcatcccac tattgtca                                       28

<210> SEQ ID NO 4
<211> LENGTH: 30
<212> TYPE: DNA

```
<213> ORGANISM: artificial
<220> FEATURE:
<223> OTHER INFORMATION: primer for human Id protein with inserted
      restriction site

<400> SEQUENCE: 4
gtggaattca acaccgtcta ttcagccaca                                      30

<210> SEQ ID NO 5
<211> LENGTH: 29
<212> TYPE: DNA
<213> ORGANISM: artificial
<220> FEATURE:
<223> OTHER INFORMATION: primer for human Id protein with inserted
      restriction site

<400> SEQUENCE: 5
ataggatcca ccttcccatc cagacagcc                                       29

<210> SEQ ID NO 6
<211> LENGTH: 30
<212> TYPE: DNA
<213> ORGANISM: artificial
<220> FEATURE:
<223> OTHER INFORMATION: primer for human Id protein with inserted
      restriction site

<400> SEQUENCE: 6
gtggaattcc ctgagcacca ggttcagtct                                      30

<210> SEQ ID NO 7
<211> LENGTH: 147
<212> TYPE: DNA
<213> ORGANISM: artificial
<220> FEATURE:
<223> OTHER INFORMATION: amplicon from human Id1

<400> SEQUENCE: 7
caccctcaac ggcgagatca gcgccctgac ggccgaggcg gcatgcgttc ctgcggacga     60
tcgcatcttg tgtcgctgaa gcgcctcccc cagggaccgg cggaccccag ccatccaggg   120
ggcaagagga attacgtgct ctgtggg                                       147

<210> SEQ ID NO 8
<211> LENGTH: 171
<212> TYPE: DNA
<213> ORGANISM: artificial
<220> FEATURE:
<223> OTHER INFORMATION: amplicon from human Id2

<400> SEQUENCE: 8
cccactattg tcagcctgca tcaccagaga cccgggcaga accagcgctc caggacgccg     60
ctgaccaccc tcaacacgga tatcagcatc ctgtccttgc aggcttctga attcccttct   120
gagttaatgt caaatgacag caaagcactg tgtggctgaa taagcggtgt t            171

<210> SEQ ID NO 9
<211> LENGTH: 241
<212> TYPE: DNA
<213> ORGANISM: artificial
<220> FEATURE:
<223> OTHER INFORMATION: amplicon from human Id3

<400> SEQUENCE: 9
accttcccat ccagacagcc gagctcgctc cggaacttgt catctccaac gacaaaagga     60
```

-continued

```
gcttttgcca ctgactcggc cgtgtcctga cacctccaga acgcaggtgc tggcgcccgt    120
tctgcctggg accccgggaa cctctcctgc cggaagccgg acggcaggga tgggcccaa     180 cttcgccctg cccacttgac ttcaccaaat cccttcctgg agactgaacc tggtgctcag    240
g                                                                    241
```

PRIMERS AND PROBES FOR AMPLIFICATION AND DETECTION OF HUMAN INHIBITOR OF DNA-BINDING

This application claims the benefit of U.S. Provisional Application No. 60/475,515, filed Jun. 3, 2003, which application is incorporated herein by reference for purposes of the US filing and all other jurisdictions permitting such incorporation.

The invention was supported with funds from NSF Grant No. IBN-9118977. The United States government may have certain rights in the invention.

BACKGROUND OF THE INVENTION

This application relates to oligonucleotide primers and nucleic acid probes that are useful for amplification and/or detection of human inhibitor of DNA-binding (Id) genetic sequences, and in particular for selective amplification and/ or detection of human Id1, Id2 and Id3.

Inhibitor of DNA-binding (Id) proteins are transcription factors and are members of a subfamily of Helix-Loop-Helix (HLH) proteins. These proteins contain a motif that consists of two segments capable of forming amphipathic alpha helices connected by a nonconserved loop. Other members of the HLH family (basic HLH, or bHLH proteins) also contain a basic region just to the amino terminal side of this motif that consists of two to three clusters of basic amino acid residues. Various proteins containing the bHLH motif can form homodimeric and heterodimeric complexes with other bHLH proteins and it is through the basic region that these complexes bind to the target DNA (Murre et al., Cell, 1989, 56, 777-783; Murre et al., Cell, 1989, 58, 537-544). The Id proteins containing the helix-loop-helix domain, but are lacking the basic region. These Id proteins are still able to form heterodimers with other bHLH transcription factors affecting transcription, but they lack DNA-binding ability and are therefore negative regulators of the bHLH transcription factors.

Four members of the Id family have been identified in mammals and the first, Inhibitor of DNA binding-1 (Id-1), originally isolated in the mouse, has been shown to exist in two forms in the human as a result of alternative splicing (Benezra et al., Cell, 1990, 61, 49-59; Deed et al., Biochim. Biophys. Acta., 1994, 1219, 160-162; Hara et al., J. Biol. Chem., 1994, 269, 2139-2145; Nehlin et al., Biochem. Biophys. Res. Commun., 1997, 231, 628-634; Zhu et al., Brain Res. Mol. Brain Res., 1995, 30, 312-326).

SUMMARY OF THE INVENTION

The present invention provides oligonucleotide primers and polynucleotide probes that provide selective amplification and detection of Id genetic sequences. Forward and reverse primer pairs for amplification of Id1, Id2 and Id3 are given in Seq. ID Nos 1 and 2, 3 and 4 and 5 and 6 respectively. These primer pairs were selected both (1) to provide the desired specificity so that they amplify only the specific Id type to which they are targeted; and (2) to introduce terminal restriction endonuclease cleavage sites into the amplicon that facilitate the incorporation of the amplicon into plasmid-based vectors. Detection of Id genetic sequences can be carried out using the labeled-amplicon by reamplifying the amplicon with the primers in the presence of labeled, for example radiolabeled, deoxy-nucleotide triphosphates. The probes of the invention correspond in sequence to the amplicon produced using the primers of the invention, after cleavage at the restriction endonuclease sites. The sequences of sense probes that correspond to wild-type human Id1, Id2, and Id3 are set forth in Seq ID Nos. 7, 8 and 9 respectively. Antisense strands of the same sequence may also be employed.

DETAILED DESCRIPTION OF THE INVENTION

The present invention relates to two types of nucleic acid polymers which are useful in the detection of human Id1, Id2 or Id3 genetic sequences. For convenience, these two types of nucleic acid polymers are referred to herein as "primers" and "probes" although it will be appreciated from the description below that the shorter "primers" can also be used in detection procedures, and that the longer "probes" can also serve as a primer for extension reactions. Thus, the names are used as labels for clarity, and there is no implication in the name that the utility of the nucleic acid polymer is in any way limited to the single function of the name.

As used in the specification and claims of this application, the term "genetic sequences" refers to either DNA or RNA sequences encoding some or all of human Id1, Id2 or Id3 protein, both in vivo and in vitro. The "genetic sequences" may be amplification products or they may be unamplified materials. The "genetic sequence" may be detected in situ to obtain maps of Id protein expression, it may be detected in a milieu of other human nucleic acids and cellular components, or it may be detected in an artificial environment, such as in host cells (prokaryotic or eukaryotic) expressing a plasmid-based vector harboring nucleic acids encoding a human Id protein.

The primers of the present invention were developed to meet several specific goals. First, each set of forward and reverse primers was designed to have little or no cross-reactivity with other Id proteins and members of the HLH family in hybridization experiments with human tissue samples. Second, the primers each include a restriction endonuclease cleavage site, such that the ends can be trimmed from amplicons produced using the primers in a PCR amplification to produce a sequence that can be readily inserted into a plasmid-based vector for cloning to produce multiple copies of the amplicon for use as a probe. Construction of oligonucleotides of defined sequence is routine and companies exist to provide requested materials. Primers of the invention can be constructed using such known techniques for synthesis of oligonucleotides.

For Id1, the primers of the invention have the sequence:

Forward:
ataggatccc accctcaacg gcgagat    Seq ID No. 1

Reverse:
gtggaattcc ccacagagca cgtaattcct    Seq ID No. 2

In each sequence, the underlined portions corresponds to the sequence of Id1, while the remainder is an introduced segment to provide the restriction endonuclease cleavage site.

For Id2, the primers of the invention have the sequence:

Forward:
ataggatccc cgcatcccac tattgtca    Seq ID No. 3

Reverse:
gtggaattca acaccgtcta ttcagccaca    Seq ID No. 4

In each sequence, the underlined portions corresponds to the sequence of Id2, while the remainder is an introduced segment to provide the restriction endonuclease cleavage site.

For Id3, the primers of the invention have the sequence:

```
Forward:
ataggatcca ccttcccatc cagacagcc      Seq ID No. 5

Reverse:
gtggaattcc ctgagcacca ggttcagtct     Seq ID No. 6
```

In each sequence, the underlined portions corresponds to the sequence of Id3, while the remainder is an introduced segment to provide the restriction endonuclease cleavage site.

These primers pairs can be used for selective amplification of Id1, Id2 or Id3 sequences using polymerase chain reaction procedures. In this case, the amplification products are suitably separated by size on a matrix such as a polyacrylamide gel and incorporated label detected. Suitable labels include without limitation radio-labels, fluorescent labels, colored labels, and fluorogenic or chromogenic labels.

The amplicons of sizes characteristic of the Id1, Id2 and Id3 genes are also used in accordance with the invention for construction of vectors which can be used in the production of the probes of the invention. The amplicons are purified (for example by purification-scale electrophoresis), digested with restriction endonucleases BamH1 and EcoR1 and cloned into a BamH1/EcoR1 site of a vector, such as a pBluescript vector (pBS-KS-). The modified vector is introduced into a suitable host, for example $E.\ coli$ in the case of pBluescript, to make multiple copies of the vector. These copies are recovered, and the probe of the invention obtained by direct reamplification of the plasmid.

The probes of the invention have lengths of 147 bp, 171 bp and 241 bp for Id1, Id2 and Id3, respectively, and the sequences as set forth in Seq. ID. Nos. 7, 8 and 9. The probes of the invention are suitably used in Northern hybridization analysis of RNA extracted from human cells that are to be assessed for the expression of one or more Id proteins. In a general sense, the probes of the invention can be used for qualitative or semi-quantitative assessment of Id mRNA levels in human tumor specimens. The specificity exhibited by these probes makes them of great utility in distinguishing between different Id family members, as well as between Id and other members of the helix-loop-helix family. Such measurements have diagnostic and prognostic value in the management of human disease.

For diagnostics, it has been observed that there are characteristic patterns of Id expression which distinguish some tumor types from corresponding normal tissues. For example, Northern analysis using the probes of the invention can be used to distinguish human rhabdomyosarcoma cells from normal primary human muscle cells. (See International Patent Publication WO97/05283 (designating the US), which is incorporated herein by reference in all jurisdictions permitting such incorporation.). Another, non-limiting example of the use to which the probes of the invention may be put is the evaluation of human brain tissue samples for the presence of astrocytomas. Deregulated Id expression has also been observed in disseminated medullablastoma, stage II/IV neuroblastoma and melanoma.

For prognostic purposes it has been observed that the presence of Id2 in neuroblastoma of children is an indicator of poor prognosis. Thus, detection of Id2 using the probes of the invention can be used as a basis for selecting a more aggressive course of therapy and for enhanced monitoring of the individual for disease recurrence. Similarly, Id1 positivity in astrocytomas and early stage lesions of the skin have been shown to signal more aggressive disease, and changes in disease treatment and management may therefore be indicated.

The probes of the invention may also be used in detection of low levels of Id in circulating tumor cells as a measure of metastatic risk in certain patient populations. High Id levels have also been observed in circulating endothelial cell precursors which are required for vascularization of certain tumors and which may be the targets of anti-angiogenic drug regimens. Monitoring of Id levels in these cells may be used for determining if a tumor is recruiting new blood vessels and therefore likely to begin metastasizing and whether angiogenic intervention is having the desired effect.

EXAMPLE 1

A PCR reaction was performed using human Id1 or human genomic DNA template and an Id1-specific primer pair (Seq. ID Nos. 1 and 2). Each reaction contained 5 ng of template, 500 ng of each of the 5' and 3' primers, 5 µl of 10× PCR mix (500 mM KCl, 100 mM Tris HCl pH 8.4, 15 mM $MgCl_2$, 1 mg/ml gelatin), 20 µM of each deoxynucleotide triphosphate and 3 units of Taq polymerase in a 50 µl reaction volume. PCR was performed for 25 cycles to produce amplicons using a standard Perkin-Elmer automated PCR machine (60° C. hybridization temperature, 72° C. extension temperature). The amplification mixtures were loaded on a polyacrylamide gel and separated by electrophoresis. The product band was excised, and the resulting gel slices were rotated at room temperature for 2 days in elution buffer (0.3 M sodium acetate, pH 8.0, 5 mM EDTA). Supernatant was removed from the rotated slices, and the slices were rinsed again in 100 µl elution buffer. The removed supernatant and the elution buffer from the rinse were pooled in to an Eppendorff tube to yield a total volume of about 400 µl. 40 µl 5M NaCl, 4 µl 1M $MgCl_2$ and 600 µl isopropyl alcohol were added to the tube which was centrifuged for 30 minutes. The resulting pellet was washed in 80% ethanol and dried under vacuum for 5 minutes. The pellet was then resuspended in 15 µl PCR sterile TE to form an amplicon solution.

The probe can now be used directly used directly to make a probe for in situ hybridization by reamplification as described above using $^{32}$P-labeled deoxynucleotide triphosphates. The reamplified, labeled probe is separated from unincorporated dNTPs using a G-50 Sephadex spin column and applied to tissue samples as described in Jen et al.

The unlabeled probe was also cloned into the BamHI+ EcoRI sites of pBluescript (KS⁻) (Stratagene) to ensure a limitless supply of template without reamplification of cDNA. 10 µl of the unlabeled amplicon solution was combined with 3 µl of 10× KGB buffer, 8 units of of BamH1, 8 units of EcoR1, and 15.5 µl of water and incubated at 37° C. for about 4 hours to cleave the BamH1 and EcoR1 restriction sites. 40 µl TE (10 mM Tris pH 7.4, 1 mM EDTA) and 40 µl phenol (pH 8.0) was added to the mix, centrifuged to recover the aqueous phase which was then applied to a G-50 Sepharose column to remove residual phenol. The material was precipitated by adding ⅒ volume of 3 M NaOAc, EtOH and centrifuged for 30 minutes.

The recovered pellet was resuspended in 10 μl PCR-sterile TE. 3 μl of this suspension was combined with BamH1/EcoR1 cut pBluescript vector (pBS-KS⁻), ATP and ligase in buffered and incubated overnight at 15° C. The ligated vector was transferred into *E. coli* strain JM109 using standard protocols. After growth, colonies harboring the ampicillin resistance marker of the Bluescript vector were selected by plating on ampicillin containing agar. Plasmids were isolated and tested for the presence of the amplicon insert. The resulting probe has the sequence given in Seq. ID No. 7.

EXAMPLE 2

A probe was created for human Id2 using an Id2-specific primer pair (Seq. ID Nos. 3 and 4) in the procedures of Example 1. The resulting probe has the sequence given in Seq. ID No. 8.

EXAMPLE 3

A probe was created for human Id3 using an Id3-specific primer pair (Seq. ID Nos. 5 and 6) in the procedures of Example 1. The resulting probe has the sequence given in Seq. ID No. 9.

EXAMPLE 4

RNA was extracted from human rhabdosarcoma cancer cell lines and primary human muscle cells (as a control). Northern analysis was performed using the procedures previously described in Benezra et al. (1990) *Cell* 61: 49-59, which is incorporated herein by reference, and the Id1, Id2 and Id3 probes (Seq. ID Nos 7-9). The observed hybridization patterns demonstrated the specificity of the probes, since the Id1 probe hybridized to a differently and correctly sized messenger, as compared to Id2 and Id3. In addition, in case of Id2, the specificity of the probe was confirmed by hybridization to an Id2 containing plasmid.

EXAMPLE 5

ID1 specific probe (Seq. ID No. 7) is used for in situ hybridization in the evaluation of sample suspected of being early stage melanoma. 6-7 micron sections are processed with [α-$^{33}$P]-labeled probes using the general procedure previously described in Lyden et al., *Nature* (*Lond*) 401: 670-677 (1999), which is incorporated herein by reference, and observed for binding of the label. Binding is indicative that the sample is early stage melanoma.

The invention claimed is:

1. A composition comprising a first primer consisting of SEQ ID NO: 1 and a second primer consisting of SEQ ID NO: 2.

2. A composition comprising a first primer consisting of SEQ ID NO: 3 and a second primer consisting of SEQ ID NO: 4.

3. A composition comprising a first primer consisting of a SEQ ID NO: 5 and a second primer consisting of a SEQ ID NO: 6.

* * * * *